United States Patent
Honda

(10) Patent No.: US 11,073,685 B2
(45) Date of Patent: Jul. 27, 2021

(54) METHOD FOR CONTROLLING THE MOVEMENT OF A VITREORETINAL VIEWING SYSTEM IN AN OPHTHALMIC SURGICAL MICROSCOPE, MICROSCOPE AND MOTION CONTROLLER FOR A MICROSCOPE

(71) Applicant: LEICA MICROSYSTEMS K.K., Tokyo (JP)

(72) Inventor: Masatoshi Honda, Tokyo (JP)

(73) Assignee: Leica Microsystems K.K., Tokyo (JP)

( * ) Notice: Subject to any disclaimer, the term of this patent is extended or adjusted under 35 U.S.C. 154(b) by 103 days.

(21) Appl. No.: 15/916,306

(22) Filed: Mar. 9, 2018

(65) Prior Publication Data

US 2018/0275385 A1    Sep. 27, 2018

(30) Foreign Application Priority Data

Mar. 27, 2017   (EP) ..................... 17163113

(51) Int. Cl.
| | |
|---|---|
| *G02B 21/02* | (2006.01) |
| *G02B 21/00* | (2006.01) |
| *A61B 3/13* | (2006.01) |
| *A61B 90/20* | (2016.01) |

(Continued)

(52) U.S. Cl.
CPC .............. *G02B 21/025* (2013.01); *A61B 3/13* (2013.01); *A61B 90/20* (2016.02); *G02B 7/001* (2013.01); *G02B 21/0012* (2013.01); *G02B 21/24* (2013.01)

(58) Field of Classification Search
CPC .. G02B 21/025; G02B 7/001; G02B 21/0012; G02B 21/24; G02B 21/00; G02B 21/02; G02B 21/36; G02B 21/22; G02B 21/244; G02B 7/023; A61B 90/20; A61B 3/13; A61B 3/14; A61B 3/10; A61F 9/007
USPC ........ 359/379, 377, 383, 392; 351/221, 205, 351/206, 214, 236; 606/2, 4, 5
See application file for complete search history.

(56) References Cited

U.S. PATENT DOCUMENTS

| | | |
|---|---|---|
| 2002/0191280 A1 | 12/2002 | Horiguchi et al. |
| 2010/0265460 A1 | 10/2010 | Mann |
| 2016/0022133 A1 | 1/2016 | Charles et al. |

FOREIGN PATENT DOCUMENTS

| | | |
|---|---|---|
| DE | 9415219 U1 | 11/1994 |
| DE | 102009037018 A1 | 2/2011 |

(Continued)

*Primary Examiner* — Jie Lei
(74) *Attorney, Agent, or Firm* — Hodgson Russ LLP

(57) ABSTRACT

The invention relates to a microscope (1), in particular an ophthalmic surgical microscope having a vitreoretinal viewing system (6), an optics carrier (14) and a support (2). The invention also relates to a method and a motion controller controlling the movement of the vitreoretinal viewing system (6). The optics carrier (14) is attached movably to the support (2). The vitreoretinal viewing system (6) in turn is attached movably to the optics carrier (14). The vitreoretinal viewing system (6) comprises a front piece (30), such as a optics carrier (14). To avoid contact of the front piece (30) with an eye (16) while the optics carrier (14) is moved for focusing a microscope lens (18), the position of the front piece (30) is automatically maintained stationary with respect to the support (2). This is obtained by controlling the vitreoretinal viewing system (6) to perform a counter movement to the movement of the optics carrier (14).

11 Claims, 1 Drawing Sheet

(51) Int. Cl.
*G02B 7/00* (2021.01)
*G02B 21/24* (2006.01)

(56) References Cited

FOREIGN PATENT DOCUMENTS

| EP | 3524136 | A1 | 8/2019 |
|---|---|---|---|
| WO | 9316631 | A1 | 9/1993 |

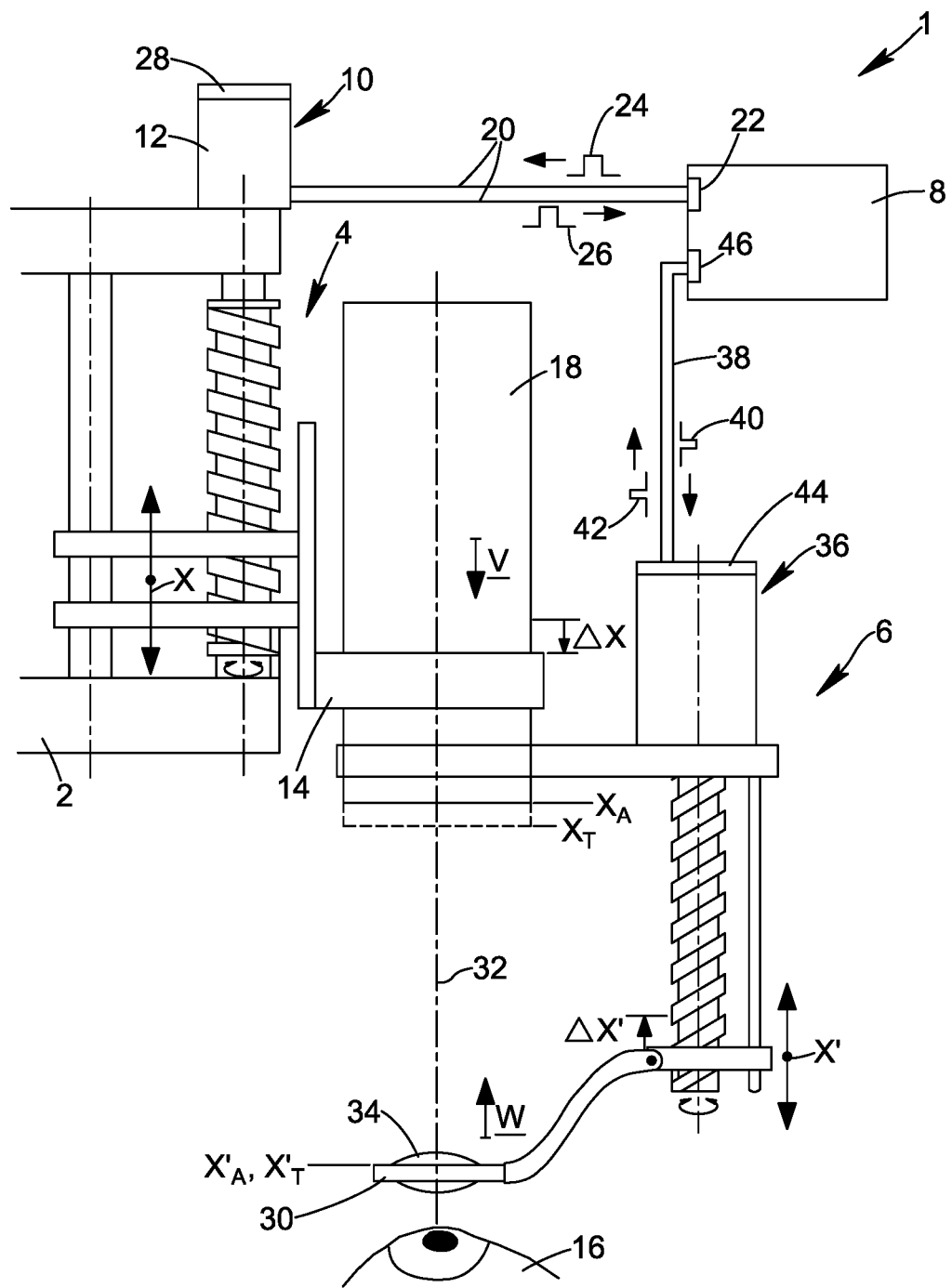

METHOD FOR CONTROLLING THE MOVEMENT OF A VITREORETINAL VIEWING SYSTEM IN AN OPHTHALMIC SURGICAL MICROSCOPE, MICROSCOPE AND MOTION CONTROLLER FOR A MICROSCOPE

CROSS REFERENCE TO RELATED APPLICATIONS

This application claims priority of European patent application number 17163113.8 filed Mar. 27, 2017, the entire disclosure of which is incorporated by reference herein.

FIELD OF THE INVENTION

The invention relates to a method for controlling the movement of a motion-controlled vitreoretinal viewing system in an ophthalmic surgical microscope, a microscope motion controller for an ophthalmic surgical microscope, and a microscope.

BACKGROUND OF THE INVENTION

The surgical ophthalmic microscope comprises a motion-controlled vitreoretinal viewing system, a motion-controlled optics carrier and a support. The optics carrier may be adapted to carry at least one microscope lens. For focusing and/or zooming, the optics carrier is moveable with respect to the support, at least in a direction towards and away from the eye. The vitreoretinal viewing system is attached to the optics carrier and is moveable with respect to the optics carrier, preferably in a direction parallel to the direction of movement of the optics carrier.

The vitreoretinal viewing system is an accessory for surgical ophthalmic microscopes and used for surgical procedures on the posterior segment of the eye. It comprises a front piece which may be configured to carry a front lens, which can be quickly exchanged after each surgery.

The front piece may be moved into the optical axis of the microscope lens mounted to the optics carrier if the vitreoretinal viewing system is used. If the vitreoretinal viewing system is not used, the front piece may be moved away from the optical axis so that it does not interfere with the microscope lens.

If the optics carrier is moved, there is a risk that the front piece contacts and thus damages or irritates the cornea of the eye. This is especially the case if the front piece is pivoted into the optical path of the lens and if the microscope lens does not have internal focus and thus has to be moved as a whole for focusing.

SUMMARY OF THE INVENTION

The goal of the present invention is therefore to devise a method and apparatus for ophthalmic surgery using a vitreoretinal viewing system that avoids contact with the eye.

For the method and microscope described above, this objective is solved by automatically maintaining the position of the front piece stationary with respect to the support of the microscope independent of a movement of the optics carrier relative to the support.

The microscope motion controller according to the invention may either be integrated into a newly manufactured microscope or be configured for retrofitting existing ophthalmic surgical microscopes. The microscope motion controller comprises an I/O section and an output section.

The I/O section is configured to output a carrier positioning signal representing a carrier target position of the optics carrier and to receive a carrier position signal representing an actual carrier position of the microscope optics carrier. The output section is configured to output a front piece positioning signal representing a front piece target position of the vitreoretinal viewing system. The motion controller is configured to compute the front piece target position from at least one of the carrier target position and the carrier actual position. The front piece target position is computed to represent a stationary position of the front piece with respect to the microscope support. The motion controller may be implemented as hardware as software, or as a combination of both hardware and software.

According to an improved embodiment, a movement of the optics carrier relative to the support is automatically compensated by a counter-movement of the front piece. The counter-movement of the front piece preferably has the same velocity as the movement of the optics carrier. The counter-movement of the front piece is preferably parallel to but directed against the movement of the optics carrier according to a further embodiment. Thus, for the vector $\underline{v}$ of the velocity of the optics carrier relative to the support and the vector $\underline{w}$ of the velocity of the vitreoretinal viewing system, the relationship $\underline{v}=-\underline{w}$ holds at least during the movement of the optics carrier. Moreover, the movement of the optics carrier and the counter-movement of the front piece may take place simultaneously. If $\underline{v}=-\underline{w}$ holds, the optics carrier and the front piece are preferably moved over the same time interval, so that the amount of movement of the front piece relative to the optics carrier compensates exactly the amount of movement of the optics carrier relative to the support.

For a simultaneous movement of both the optics carrier and the vitreoretinal viewing system, the carrier and front piece second positioning signals in the microscope motion controller may be simultaneously output at the I/O section and the output section.

The invention is also directed towards a non-transitory computer storage medium storing a program causing a computer to execute the above described method.

BRIEF DESCRIPTION OF THE DRAWING VIEW

In the following, the invention is described using an exemplary embodiment with reference to the accompanying drawing. It is to be understood that features that are described above and not shown in the embodiment, are added if the technical effect of that particular feature is advantageous for that specific application. In turn, a feature of the embodiment can be omitted for a specific application, if the technical effect of that particular feature is not needed.

FIG. 1 shows a schematic side view onto a part of a surgical ophthalmic microscope.

DETAILED DESCRIPTION OF THE INVENTION

In FIG. 1, parts of an ophthalmic surgical microscope 1 are shown, namely a support 2 comprising e.g. a stand (not shown) of the microscope for placing the microscope stably onto a floor or a table, a lens positioning system 4, a vitreoretinal viewing system 6 and a motion controller 8.

The lens positioning system 4 comprises a drive system 10 with an electric motor 12. The electric motor 12 drives a motion-controlled optics carrier 14 relative to the support in a direction x, i.e. towards or away from an observation area 15. During surgery, an eye 16 is located in the observation area 15. The optics carrier 14 is configured to support an optical device such as a microscope lens 18 providing a specific magnification or in the case of a zoom lens, a specific range of magnification. The microscope lens 18 may in particular be a lens which does not have internal focusing. Thus, for adjusting the focus of the lens 18, the optics carrier 14 must be moved in the direction x. This movement is controlled by the motion controller 8

The drive system 10 is connected via at least one data exchange lines 20 to an I/O section 22 of the motion controller. Via the at least one data exchange line 20, a carrier positioning signal 24 representing a carrier target position $x_T$ relative to the support is output from the I/O section 22 to the drive system 10. The positioning signal 24 in its simplest form may be analog, e.g. be an electric current which is output to drive the electric motor 12 until the carrier target position $x_T$ is reached. A more complicated position signal 24 may be a digital signal conforming to a bus lens communication standard.

The I/O section 22 is further configured to receive a carrier position signal 26 which is representative for the actual position $x_A$ of the optics carrier 14 relative to the support 2. The carrier position signal 26 may be generated by a position measurement device 28 such as a rotary encoder.

The vitreoretinal viewing system 6 comprises a front piece 30, which can be moved into the region between the optics carrier 14, and the eye 16. In particular, the front piece 30 may be moved into the optical axis 32 of the lens 18. The front piece 30 may be a lens holder which supports an exchangeable lens 34.

The vitreoretinal viewing system 6 is attached to the optics carrier 14 either directly, or indirectly by being mounted on the microscope lens 18. The vitreoretinal viewing system 6 is motion controlled by the motion controller 8. It comprises a drive system 36 for moving the front piece 30 in a direction x' parallel to the direction x. The vitreoretinal system 6 can be driven independently of the optics carrier 14. The drive system 36 comprises an electric motor 12.

The drive system 36 is connected to the motion controller 8 via at least one data exchange line 38. As with the data exchange line 20, the data exchange line 38 may be wired, wireless, or a combination of wired and wireless. A front piece positioning signal 40 is sent via the at least one data exchange line from the motion controller 8 to the drive system 36. The front piece positioning signal 40 may be an analog or digital signal. The front piece positioning signal 40 is representative for a target front piece position $x'_T$ to which the front piece 30 is to be driven relative to the optics carrier 14. The target front piece position $x'_T$ is measured relative to the optics carrier 14, whereas the corresponding target front piece position $x_{FT}$ is measured relative to the support 2.

A front piece position measuring device 44, such as a rotary encoder, may be provided to generate a front piece position signal 42 which is representative of the actual position $x'_A$ of the front piece relative to the optics carrier 14 and/or of the actual position $x_{FA}$ relative to the support 2. The motion controller 8 comprises an output section 46 to make available the front piece positioning signal 40 to any device connected to the output section, such as the drive system 36. The output section 46 may, however, also be configured to receive the front piece position signal 42. The motion controller 8 is configured to compute the front piece positioning signal 42 depending on at least one of the carrier position signal 24 and the carrier position signal 26.

As can be seen from FIG. 1, there is a risk that the front piece 30 contacts the eye 16 if the optics carrier 14, or the microscope lens 18 respectively, is moved towards the eye 16, and the distance between the optics carrier 14 and the front piece 30 is kept constant.

To avoid this, the front piece 30 is, in at least one mode of operation of the microscope 1 and/or the motion controller 8, kept stationary relative to the support 2 independent of the movement of the optics carrier 14, or the microscope lens 18 respectively.

This is realized in that an amount of movement $\Delta x$ of the optics carrier 14 in direction x relative to the support 2 is countered by an equal but opposite amount of movement $\Delta x'$, $\Delta x = -\Delta x'$, of the front piece 30 in direction x' relative to the support 2. In particular, the velocity $\underline{v}$ of the optics carrier 14, or the microscope lens 18 respectively, relative to the support 2 may be of the same magnitude but of opposite direction as the velocity $\underline{w}$ of the front piece 30 relative to the optics carrier 14, or the microscope lens 18, respectively, i.e. $\underline{v} = -\underline{w}$. This means, that for any time while this relation holds, the actual velocity of the front piece 30 relative to the support is zero, i.e. the front piece 30 is held stationary. For this, the optics carrier 14, or the lens 18 respectively, and the front piece 30 are driven simultaneously by their respective motors 12, 37. This motion compensation may take place independently of the direction, in which the optics carrier 14 is driven. Alternatively, the motion compensation may take place only if the optics carrier is moved towards the observation region 15 as there is a risk of the front piece 30 contacting the eye 16 only in this direction of movement.

Of course, the microscope 1 or the motion controller 8 respectively, may be switched into another mode, where the front piece 30 may be moved differently, so that the actual position $x_{FA}$ of the front piece 30 changes with respect to the support 2.

REFERENCE NUMERALS 1 ophthalmic surgical microscope
2 support
4 lens positioning system
6 vitreoretinal viewing system
8 motion controller
10 drive system of lens positioning system
12 motor
14 optics carrier
15 observation area
16 eye
18 microscope lens
20 data exchange line
22 I/O section of motion controller
24 carrier positioning signal
26 carrier position signal
28 carrier position measurement device
30 front piece
32 optical access of microscope lens
34 lens in front piece
36 drive system of vitreo retinal viewing system
37 motor
38 data exchange line
40 front piece positioning signal
42 front piece position signal
44 front piece position measurement device
46 output section of motion controller
x direction of movement of lens positioning system relative to support x' direction of movement of front piece relative to optics carrier
$x_A$ actual position of lens positioning system relative to support
$x_T$ target position of lens positioning system relative to support
$x'_T$ target position of front piece relative to optics carrier
$x'_A$ actual position of front piece relative to optics carrier
$x_{FT}$ target position of front piece relative to support
$x_{FA}$ actual position of front piece relative to support
$\underline{v}$ velocity vector of movement of optics carrier relative to support
$\underline{w}$ velocity vector of movement of front piece relative to optics carrier

What is claimed is:

1. A method for controlling the movement of a motion-controlled vitreoretinal viewing system (6) in an ophthalmic surgical microscope (1) comprising a movable motion-controlled optics carrier (14) to which the vitreoretinal viewing system (6) is attached movably, at least one microscope lens (18) carried by the optics carrier (14), wherein none of the at least one microscope lens (18) is movable relative to the optics carrier (14) or relative to another of the at least one microscope lens (18) such that the optics carrier (14) does not have internal focusing to adjust a focus of the at least one microscope lens (18), and the at least one microscope lens (18) must be moved with the optics carrier (14) as a whole to adjust the focus of the at least one microscope lens (18), and a microscope support (2) to which the optics carrier (14) is attached movably, the vitreoretinal viewing system (6) comprising a front piece (30), the method comprising:

moving the optics carrier (14) as a whole to adjust the focus of the at least one microscope lens (18) while automatically maintaining a position of the front piece (30) stationary with respect to the support (2) as the optics carrier (14) is moved.

2. The method according to claim 1, wherein a movement (Δx) of the optics carrier (14) is automatically compensated by a counter-movement (Δx') of the front piece (30).

3. The method according to claim 2, wherein the front piece (30) is moved with a velocity ($\underline{w}$) relative to the optics carrier (14), the amount of the velocity ($\underline{w}$) corresponding to the amount of a velocity ($\underline{v}$) with which the optics carrier (14) is moved relative to the support (2), the direction of the velocity ($\underline{w}$) of the front piece (30) being opposite to the direction of the velocity ($\underline{v}$) of the optics carrier (14).

4. The method according to claim 2, wherein the front piece (30) and the optics carrier (14) are moved simultaneously.

5. A non-transitory computer storage medium storing a program causing a computer to execute the method according to claim 1.

6. A microscope motion controller (8) for an ophthalmic surgical microscope (1) comprising an optics carrier (14), at least one microscope lens (18) carried by the optics carrier (14), wherein none of the at least one microscope lens (18) is movable relative to the optics carrier (14) or relative to another of the at least one microscope lens (18) such that the optics carrier (14) does not have internal focusing to adjust a focus of the at least one microscope lens (18), and the at least one microscope lens (18) must be moved with the optics carrier (14) as a whole to adjust the focus of the at least one microscope lens (18), a microscope support (2) to which the optics carrier (14) is attached movably, and a vitreoretinal viewing system (6) attached movably to the optics carrier (14) and having a front piece (30), the motion controller (8) comprising:

an I/O section (22) configured to output a carrier positioning signal (24) representing a carrier target position of the optics carrier (14) and to receive a carrier position signal (26) representing an actual carrier position of the optics carrier (14); and an output section (46) configured to output a front piece positioning signal (40) representing a front piece target position of the vitreoretinal viewing system (6);

wherein the motion controller (8) is configured to compute the front piece target position from at least one of the carrier target position and the carrier actual position, the front piece target position relative to the support (2) being constant.

7. The microscope motion controller (8) according to claim 6, wherein the carrier positioning signal (24) and the front piece positioning signal (40) are simultaneously output at the I/O section (22) and the output section (46).

8. An ophthalmic surgical microscope (1) comprising:
a support (2);
an optics carrier (14) adapted to carry at least one microscope lens (18) and attached movably to the support (2);
at least one microscope lens (18) carried by the optics carrier (14), wherein none of the at least one microscope lens (18) is movable relative to the optics carrier (14) or relative to another of the at least one microscope lens (18) such that the optics carrier (14) does not have internal focusing to adjust a focus of the at least one microscope lens (18), and the at least one microscope lens (18) must be moved with the optics carrier (14) as a whole to adjust the focus of the at least one microscope lens (18); and
a vitreoretinal viewing system (6) attached movably to the optics carrier (14), the vitreoretinal viewing system (6) comprising a front piece (30);
wherein, in at least one mode of operation of the microscope (1), a position of the front piece (30) is stationary relative to the support (2) while the optics carrier (14) is moved relative to the support (2) to adjust the focus of the at least one microscope lens (18).

9. The microscope (1) according to claim 8, wherein the front piece (30) comprises a lens holder.

10. The microscope (1) according to claim 8, wherein the microscope (1) comprises an observation area (15) in which an eye (16) is located during operation of the microscope (1), and wherein the front piece (30) is arranged between the observation area (15) and the optics carrier (14).

11. The microscope (1) according to claim 8, wherein the vitreoretinal viewing system (6) and the optics carrier (14) are motion-controlled, and the microscope (1) further comprises a motion controller (8) configured to automatically maintain a position of the front piece (30) stationary with respect to the support (2) while the optics carrier (14) is moved relative to the support (2).

* * * * *